United States Patent
Rosthauser et al.

(10) Patent No.: US 7,030,274 B2
(45) Date of Patent: Apr. 18, 2006

(54) PROCESS FOR THE PRODUCTION OF CARBODIIMIDE MODIFIED ORGANIC ISOCYANATES

(75) Inventors: James William Rosthauser, Pittsburgh, PA (US); James Thomas Garrett, McKees Rocks, PA (US); Jeffrey S. Bolton, Baytown, TX (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 0 days.

(21) Appl. No.: 10/870,088

(22) Filed: Jun. 17, 2004

(65) Prior Publication Data

US 2005/0282993 A1     Dec. 22, 2005

(51) Int. Cl.
*C08G 18/02*     (2006.01)

(52) U.S. Cl. .................. 564/252; 252/182.21; 548/952; 528/44

(58) Field of Classification Search ................ 564/252; 252/182.21; 548/952
See application file for complete search history.

(56) References Cited

U.S. PATENT DOCUMENTS

| | | | |
|---|---|---|---|
| 2,853,473 A | 9/1958 | Campbell et al. | 260/77.5 |
| 3,516,950 A | 6/1970 | Haggis | 260/25 |
| 3,793,382 A | 2/1974 | Kolakowsid et al. | 260/453 SP |
| 4,014,935 A * | 3/1977 | Ibbotson | 540/202 |
| 4,814,103 A | 3/1989 | Potter et al. | 252/182.22 |
| 4,937,012 A | 6/1990 | Kan et al. | 252/182.21 |
| 5,202,358 A | 4/1993 | Scholl et al. | 521/160 |
| 5,342,881 A | 8/1994 | Müller et al. | 524/700 |
| 5,610,408 A | 3/1997 | Imokawa et al. | 252/182.2 |
| 5,726,240 A | 3/1998 | Rosthauser et al. | 524/590 |
| 5,783,652 A | 7/1998 | Rosthauser et al. | 528/48 |
| 6,120,699 A | 9/2000 | Narayan et al. | 252/182.2 |
| 6,127,463 A | 10/2000 | Adkins et al. | 524/114 |
| 6,166,128 A | 12/2000 | Adkins et al. | 524/589 |
| 6,362,247 B1 | 3/2002 | Brown | 521/160 |
| 6,489,503 B1 | 12/2002 | Narayan et al. | 560/26 |
| 6,528,609 B1 | 3/2003 | Adkins et al. | 528/59 |

FOREIGN PATENT DOCUMENTS

EP     0 193 787     9/1986

* cited by examiner

*Primary Examiner*—Rachel Gorr
(74) *Attorney, Agent, or Firm*—Joseph C. Gil; Lyndanne M. Whalen; N. Denise Brown

(57) ABSTRACT

The present invention relates to an improved process for the production of carbodiimide modified organic isocyanate, preferably a polymethylene polyphenylisocyanate, and most preferably diphenylmethane diisocyanate. This process includes (1) neutralizing acidic impurities in an organic isocyanate, (2) partially carbodiimidizing isocyanate groups of the neutralized organic isocyanate, and (3) terminating the carbodiimidization reaction.

21 Claims, No Drawings

PROCESS FOR THE PRODUCTION OF CARBODIIMIDE MODIFIED ORGANIC ISOCYANATES

BACKGROUND OF THE INVENTION

The present invention relates to an improved process for the preparation of carbodiimide modified organic isocyanate, preferably polyphenylmethane polyisocyanates, and most preferably diphenylmethane diisocyanates. This process comprises (1) neutralizing acidic impurities in an organic isocyanate, (2) partially carbodiimidizing isocyanate groups of the neutralized organic isocyanate, (3) terminating the carbodiimidization reaction.

Carbodiimidization of isocyanates is known and described in, for example, U.S. Pat. Nos. 2,853,473, 4,937,012, 5,202,358, 5,610,408, 6,120,699, 6,362,247, and 6,489,503, and in EP 193,787. Carbodiimidization of isocyanates is desirable to provide storage stable liquids. Liquids are easier to pump and less expensive to transport than fused solids or slurries. The liquids are homogeneous compositions as supplied without the need to homogenize as with slurries or fused solids. In the production of polyurethanes, a liquid can be added easily by weight or volume and combined with suitable co-reactants at room temperature. This is safer than using the materials at elevated temperature and the corresponding higher vapor pressure of the heated materials.

Methods for improving stability and/or reactivity of polyisocyanates are also known and described in the art. See U.S. Pat. Nos. 3,793,362, 5,342,881, 5,726,240, 5,783,652 and 6,528,609. Most of these patents disclose blending or mixing an organic polyisocyanate with an epoxide or other compound.

Many of these methods describe improving the reactivity of polymer MDI or adducts prepared from MDI that initially have adicity values that well exceed 25 ppm as measured using ASTM D 5629. By comparison, the refined starting materials described in the present invention typically have acidity values well under 25 ppm. Due to the extremely low levels of highly efficient catalyst used in the preparation of the carbodiimides described in the present invention and to the sensitivity of these catalysts to acidic impurities, it is necessary to remove even this low amount of acidity.

Normally, the acidity of the isocyanate can be lowered to levels below 25 ppm by distillation. Depending on the efficiency of the columns used in the distillation process, these levels can be reduced to a range of 1–10 ppm. Trace levels of hydrogen chloride or hydrolysable chloride can be further removed by heating the isocyanate and passing an inert gas through the materials during distillation as in U.S. Pat. No. 3,516,950.

U.S. Pat. Nos. 4,814,103, 6,127,463 and 6,166,128 disclose that the color of various organic polyisocyanates can be stabilized and/or reduced by the addition of epoxides alone or in combination with hindered phenols.

Copending application Ser. No. 10/870/126, filed in the U.S. Patent and Trademark Office on Jun. 17, 2004, the same day as the present application, and which is commonly assigned, relates to TDI prepolymers with improved processing characteristics. These TDI prepolymer compositions comprise from about 95 to about 99.99% by weight of a prepolymer of toluene diisocyanate, and from about 0.01 to about 5% by weight of an epoxide having an epoxide equivalent weight of from about 44 to about 400. The prepolymer of TDI comprises the reaction product of toluene diisocyanate containing from about 60 to about 100% by weight of the 2,4-isomer and from about 0 to about 40% by weight of the 2,6-isomer, and an isocyanate-reactive component having a functionality of from about 1.5 to about 8 and an OH number of from about 14 to about 1870.

Advantages of the present invention include lower color of the carbodiimide polyisocyanate product due to quicker processing to form the carbodiimide. The resulting products can be produced using lower levels of carbodiimidization catalyst so that the stability of the final product is improved. Also, the lower amount of catalyst requires less catalyst stopper which is advantageous since catalyst stopper can cause yellowing of the final product.

SUMMARY OF THE INVENTION

This invention relates to an improved process for the preparation of carbodiimide modified polymethylene polyphenylisocyanates, including those carbodimiide modified polymethylene polyisocyanates which contain uretonimine groups. This process comprises: (1) neutralizing acidic impurities in an organic isocyanate, preferably a polyisocyanate of the diphenylmethane series, with an acid scavenger, (2) partially carbodiimidizing isocyanate groups of the neutralized organic isocyanate with a catalyst of the phosphorous oxide type, and (3) terminating the carbodiimidization reaction by addition of an acid or other suitable poison.

In accordance with the present invention, the process may also comprise (1) partially carbodiimidizing isocyanate groups of an organic isocyanate with a catalyst of the phosphorous oxide type, (2) neutralizing acidic impurities in the partially carbodiimidized isocyanate by addition of an acid scavenger, and (3) terminating the carbodimiidization reaction reaction by addition of an acid stopper or other suitable poison.

In a preferred embodiment, the process of the present invention also inherently forms uretonimine groups in the carbodiimidized isocyanate. Almost all of the above prepared carbodiimide modified isocyanate groups form uretonimine groups at room temperature. In the presence of excess isocyanate groups, carbodiimides rapidly form uretonimine groups. The equilibrium favors the uretonimine at room temperature. The uretonimine is less favored at elevated temperatures and regenerates isocyanate and carbodiimide.

The present invention also relates to liquid stable organic isocyanates containing carbodiimide groups and/or uretonimine groups. These isocyanates preferably have an NCO group content of from about 23 to about 32%, and preferably comprise (1) one or more diphenylmethane diisocyanates and/or higher homologues of the MDI series (i.e. polymethylene polyphenylisocyanates), and (2) one or more epoxide.

The isocyanates of the present invention have an NCO group content of from about 23 to about 32% and comprise (1) from about 60 to less than 90% by weight of MDI, (2) from 10 to 40% by weight of carbodiimide and/or uretonimine, and (3) epoxide. The amount of epoxide present in the composition is relatively small. The sum of the %'s by weight of (1), (2) and (3) totals 100% by weight of the isocyanate.

DETAILED DESCRIPTION OF THE INVENTION

Any organic isocyanates may be used as starting materials for the process according to the invention. However, the process according to the invention is preferably used for the carbodiimidization of organic diisocyanates of the type used in polyurethane chemistry. Suitable polyisocyanates which may be used in forming the isocyanate compositions in accordance with the present invention include monomeric diisocyanates, and polyisocyanates. Suitable monomeric diisocyanates may be represented by the formula R(NCO)$_2$ in which R represents an organic group obtained by removing the isocyanate groups from an organic diisocyanate having a molecular weight of about 56 to 1,000, preferably about 84 to 400. Diisocyanates preferred for the process according to the invention are those represented by the above formula in which R represents a divalent aliphatic, hydrocarbon group having 4 to 12 carbon atoms, a divalent cycloaliphatic hydrocarbon group having 6 to 13 carbon atoms, a divalent araliphatic hydrocarbon group having 7 to 20 carbon atoms or a divalent aromatic hydrocarbon group having 6 to 18 carbon atoms. Preferred monomeric diisocyanates are those wherein R represents an aromatic hydrocarbon group.

Examples of the suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis(4-isocya-natocyclohexyl) methane, 2,4'-dicyclohexylmethane diisocyanate, 1,3- and 1,4-bis(isocyanatomethyl)cyclohexane, bis(4-isocyanato-3-methyl-cyclohexyl) methane, α,α, α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluene diisocyanate, 1,3- and/or 1,4-phenylene diisocyanate, 2,4- and/or 2,6-toluene diisocyanate, 2,2'-, 2,4'- and/or 4,4'-diphenylmethane diisocyanate, 1,5-diisocyanato naphthalene and mixtures thereof. Aromatic polyisocyanates containing 3 or more isocyanate groups such as 4,4',4"-triphenylmethane triisocyanate and polymethylene poly(phenylisocyanates) obtained by phosgenating aniline/formaldehyde condensates may also be used.

Suitable di- and/or polyisocyanates to be in accordance with the present invention typically have NCO group contents from about 25 to about 50%. These di- and/or polyisocyanates typically have NCO group contents of at least about 25%, preferably at least about 30% and most preferably at least about 33%. The polyisocyanates suitable herein also typically have NCO group contents of less than or equal to 50%, preferably of less than or equal to 40% and most preferably of less than or equal to 34%. The polyisocyanates may have an NCO group content ranging between any combination of these upper and lower values, inclusive, e.g., from 25 to 50%, preferably from 30 to 40% and most preferably from 31 to 34%.

The most suitable organic polyisocyanates of the present invention are based on diphenylmethane diisocyanates and polyphenylmethane polyisocyanates which have the above disclosed NCO group contents. It is preferred that the polyisocyanate component comprise 100% by weight of purified diphenylmethane diisocyanate and 0% by weight of polyphenylmethane polyisocyanate, with the sums totaling 100% of the polyisocyanate.

These polyisocyanates typically have a monomeric MDI content of at least about 60%, preferably of at least about 75%, more preferably of at least about 90% and most preferably of at least about 98%. The polyisocyanates also typically have a monomeric MDI content of less than or equal to about 100%. These polyisocyanates may have a monomeric MDI content ranging between any combination of these upper and lower values, inclusive, e.g., from 60 to 100%, preferably from 75 to 100%, more preferably from 90 to 100%, and most preferably from 98 to 100%.

In addition, these polyisocyanates typically have a polymeric MDI content of at least about 0%. The polyisocyanates also typically have a polymeric MDI content of less than or equal to about 40%, preferably less than or equal to about 25%, more preferably less than or equal to about 10% and most preferably less than or equal to about 2%. These polyisocyanates may have a polymeric MDI content ranging between any combination of these upper and lower values, inclusive, e.g., from 0 to 40%, preferably from 0 to 25%, more preferably from 0 to 10% and most preferably from 0 to 2%. Obviously, when polymeric MDI is present, the sum of the monomeric MDI content and of the polymer MDI content totals 100% by weight of the MDI.

Suitable polyisocyanates of the above described monomeric MDI contents, typically have an isomer distribution of 2,2'-, 2,4'- and 4,4'-MDI as follows. The % by weight of (1) the 2,4'-isomer of diphenylmethane diisocyanate is typically at least about 0%. The % by weight of (1) the 2,4'-isomer generally is about 60% or less, preferably about 10% or less, more preferably about 2% or less and most preferably about 1% or less. The diphenylmethane diisocyanate component may have (1) a 2,4'-isomer content ranging between any of these upper and lower values, inclusive, e.g., from 0 to 60%, preferably from 0 to 10%, more preferably from 0 to 2% and most preferably from 0 to 1% by weight. The % by weight of the (2) 2,2'-isomer of diphenylmethane diisocyanate is typically at least about 0%. The % by weight of (2) the 2,2'-isomer generally is about 6% or less, preferably 1% or less, more preferably about 0.2% or less and most preferably about 0.1% or less. The diphenylmethane diisocyanate component may have (2) a 2,2'-isomer content ranging between any of these upper and lower values, inclusive, e.g., from 0 to 6%, preferably from 0 to 1%, preferably from 0 to 0.2%, and most preferably from 0 to 0.1% by weight. The % by weight of (3) the 4,4'-isomer of diphenylmethane diisocyanate is typically at least about 34%, preferably at least about 80%, more preferably at least about 96%, and most preferably at least about 98%. The % by weight of (3) the 4,4'-isomer generally is about 100% or less. The diphenylmethane diisocyanate component may have (3) a 4,4'-isomer content ranging between any of these upper and lower values, inclusive, e.g., from 34 to 100%, preferably from 80 to 100%, more preferably from 96 to 100%, and most preferably from 98 to 100% by weight. It is particularly preferred that the diphenylmethane diisocyanate component comprise 100% by weight of the 4,4'-isomer. The sum of the %'s by weight of the isomers (1), (2) and (3) totals 100% by weight of the monomeric diphenylmethane diisocyanate.

A particularly suitable isocyanate component for the present invention comprises 80 to 100% by weight of diphenylmethane diisocyanate and 0 to 20% by weight of higher functional polyisocyanates of the diphenylmethane series, wherein the diphenylmethane diisocyanate comprise from 40 to 80% by weight of the 4,4'-isomer, from 0 to 8% by weight of the 2,2'-isomer and from 20 to 60% by weight of the 2,4'-isomer, with the sum of the %'s by weight of the 4,4'-isomer, the 2,2'-isomer and the 2,4'-isomer totaling 100% by weight of the monomeric diphenylmethane diisocyanate.

Another particularly suitable isocyanate for the present invention comprises 90 to 100% by weight of diphenylmethane diisocyanate and 0 to 10% by weight of higher functional polyisocyanates of the diphenylmethane series, wherein the diphenylmethane diisocyanate comprise from 96 to 100% by weight of the 4,4'-isomer, from 0 to 1% by weight of the 2,2'-isomer and from 0.1 to 4% by weight of the 2,4'-isomer, with the sum of the %'s by weight of the 4,4'-isomer, the 2,2'-isomer and the 2,4'-isomer totaling 100% by weight of the monomeric diphenylmethane diisocyanate.

Another particularly suitable isocyanate for the present invention comprises 100% by weight of diphenylmethane diisocyanate, with the diphenylmethane diisocyanate comprising from 96 to 100% by weight of the 4,4'-isomer, from 0 to 1% by weight of the 2,2'-isomer and from 0.1 to 4% by weight of the 2,4'-isomer, with the sum of the %'s by weight of the isomers totaling 100% by weight of the monomeric diphenylmethane diisocyanate.

Suitable compounds to be used as acid scavengers in the present invention include compounds such as, for example, pure metals, salts and oxides of, for example, zinc, magnesium, sodium, calcium, aluminum, and mixtures thereof; any carboxylic acid salt as described in, for example, U.S. Pat. No. 4,272,441, the disclosure of which is herein incorporated by reference; basic solid materials in particulate form including compounds such as, for example, sodium carbonate, sodium bicarbonate, calcium carbonate, calcium oxide, potassium carbonate, potassium bicarbonate; basic materials absorbed onto or grafted onto insoluble resin matrices, for example, amine compounds grafted onto crosslinked polystyrene; epoxides such as liquid epoxides including liquid aliphatic epoxides, epoxidized oils including, for example, epoxidized dimer and trimer fatty acids, epoxidized mono- di- and triglycerides including those of vegetable or animal origin; etc.

Among the suitable active metal-containing acid scavengers are included compounds selected from the group consisting of sodium stearate, magnesium stearate, zinc stearate; magnesium or magnesium/zinc hydrotalcites, optionally coated with 5 to 50% of metal stearate; zinc oxide, zinc hydroxide, calcium oxide, calcium hydroxide, magnesium oxide and magnesium hydroxide, and compounds such as, for example, L-55 R: hydrotalcite, a magnesium aluminum hydroxide carbonate hydrate, coated with 18% sodium stearate, available from Reheis Inc, Berkeley Heights, N.J., USA, and Hysafe 510: a magnesium hydrotalcite, available from J. M. Huber Corp., Havre de Grace, Md., USA. Other suitable acid scavengers are disclosed in U.S. Pat. No. 6,593,485, the disclosure of which is herein incorporated by reference.

Suitable acid scavengers for present invention also include solvent soluble salts including cadmium laurate, cobaltic benzoate, ferric naphthanate and the like as described in, for example, U.S. Pat. No. 3,264,336, the disclosure of which is herein incorporated by reference. Also suitable are the solid hydrotalcites and amorphous basic aluminum magnesium carbonates, such as those described in U.S. Pat. Nos. 4,427,816, 5,106,898, 5,234,981 and 6,225,387, the disclosures of which are herein incorporated by reference.

The most preferred materials within the active metal-containing compounds, are the metals, the oxides and the carboxylic acid salts. It should be noted further that the oxides must be utilized at a smaller concentration than the salts. If the oxides are utilized at somewhat above their ranges disclosed below, then what happens is that they inhibit the cure of the composition and the composition based on the carbodiimide and polyol coreactants will cure slowly if at all, depending on how much of the materials has been placed in the composition. It must be noted that preferably there is utilized the foregoing materials of zinc, aluminum and magnesium as acid scavengers in the instant composition. The carboxylic acid salts of zinc and magnesium, operate in the present invention and the oxides of these metals should also operate within the scope of the present invention as acid scavengers.

Among the suitable materials of zinc, sodium, calcium, potassium, aluminum and magnesium as acid scavengers in the instant composition are the carboxylic acid salts of zinc and magnesium, and the oxides of these metals. Accordingly, only slightly basic or amphoteric metals would be desirable and/or suitable as acid scavengers in the instant invention. If the material is slightly basic or amphoteric it will absorb the acid that is given off during the hydrolysis to form an innocuous salt without detracting from the final cured properties of the composition. Accordingly, zinc, magnesium and aluminum compounds will function effectively in the instant case even as zinc and magnesium metals. Aluminum and/or sodium metal might also function effectively as acid scavengers. Metal powders can function effectively as acid scavengers, however, they are more difficult to use as acid scavengers due to their pyrophoric nature. Such suitable acid scavengers are known and described in, for example, U.S. Pat. No. 4,680,363, the disclosure of which is hereby incorporated by reference.

Acidity can be neutralized from the isocyanate by contacting it with these basic substances that are in the solid state. In a typical embodiment, the process of the present invention may be carried out in both batch and continuous modes. Slurries of the solid materials in the liquid isocyanate starting materials are stirred and the solid is subsequently removed by filtration. In a batch mode operation, the use of agitation may be beneficial in improving base efficiency. Typical means of agitation include the use of mechanical stirrers at speeds ranging from about 400 to about 1200 rpm. Lime or sodium carbonate has been suggested to be used as in U.S. Pat. No. 3,793,362, the disclosure of which is hereby incorporated by reference.

If the neutralizing compound is extremely efficient, the solid material can be loaded into a column and the liquid isocyanate or isocyanate solution is passed through the column. In a continuous mode of operation, a fixed bed of solid material may be used and product to be treated pumped through the bed. These processes may be run over a wide range of temperatures from about 40 to about 200° C. Preferably the temperature range is from about 40 to about 100° C., and most preferably from about 60 to about 90° C. The pressure of the system should be in the range of 20 to 75 psig. Suitable solid materials for these processes are commercially available ion exchange resins that contain basic groups including but not limited to tertiary amines. One such of these materials is available from Rohm and Haas under the product tradename Amberlite IRA900 or from Sybron Chemicals as Lewatit MonoPlus MP 500.

Both of these methods are less preferred because it is difficulat to remove the solids efficiently and the solid materials containing residual isocyanate must be treated as hazardous water.

Any chemical compound which contains the epoxide (oxirane) functionality is most suitable as the acid scavenger in the present invention. These materials are soluble in the isocyanates and remain in the final carbodiimide product. The term "epoxide" or "epoxy" as used herein refers to any organic compound or resin containing at least one group comprising a three membered oxirane ring. Preferably two or more oxirane groups are present in the epoxide compound or resin in order to obtain the polyisocyanate compositions with consistent reactivity profiles of the instant invention. The epoxide equivalent weight (EEW) range of suitable epoxides is from about 44 to 400, preferably 100 to 350 and most preferably 150 to 300. Both aromatic and aliphatic polyepoxides may be used, and are well known. Suitable epoxies are described in U.S. Pat. No. 5,726,240, the disclosure of which is hereby incorporated by reference.

It is somewhat less preferred that the epoxy comprises an aromatic polyepoxide due to the tendency of them to cause yellowing as well as their reduced efficacy. Examples of such aromatic polyepoxides include but are not limited to those selected from the group consisting of the polyglycidyl ethers of polyhydric phenols; glycidyl esters of aromatic carboxylic acids; N-glycidylaminoaromatics such as N-glycidylamino-benzene, N,N,N',N'-tetraglycidyl-4,4'-bis-aminophenyl methane, and diglycidylaminobenzene; glycidylamino-glycidyloxyaromatics such as glycidylaminoglycidyloxybenzene; and mixtures thereof.

The aromatic polyepoxide resins, comprised of the polyglycidyl-ethers of polyhydric phenols including bis(phenol A), are also less preferred because they contain hydroxyl groups and thus, react with the polyisocyanate mixtures. Thus, this reduces the isocyanate content. Also, less preferred are aliphatic epoxides containing hydroxyl groups, e.g., glycidol, for the same reason. The preferred epoxides for use according to the invention are the aliphatic epoxides which do not contain hydroxyl groups.

Suitable for use are $C_2$–$C_{18}$ aliphatic epoxides such as, for example, ethylene oxide, propylene oxide, 1,2-butene oxide, 2,3-butene oxide (cis and/or trans), isobutylene oxide, 1,2-pentene oxide, 2,3-pentene oxide, cyclopentene oxide, 1,2-hexene oxide, cyclohexene oxide, and the like and mixtures thereof.

Examples of useful aliphatic polyepoxides include but are not limited to those selected from the group consisting of vinyl cyclohexene dioxide; butadiene dioxide, triglycidyl isocyanurate; and those containing ether linkages such as triglycidyl pentaerythritol, tetraglycidyl pentaery-thritol, diglycidylethers of cylcohexane dimethanol and the diglycidylethers of other diols known to those skilled in the art, 1,4-bis(2,3-epoxypropoxy)-benzene; 1,3-bis(2,3-epoxypropoxy)benzene; 4,4'-bis(2,3-epoxypropoxy)-diphenyl ether; 1,8-bis(2,3-epoxypropoxy)octane; 1,4-bis(2,3-epoxypropoxy)cyclohexane; 4,4'-(2-hydroxy-3,4-epoxybutoxy)-diphenyl dimethyl methane; 1,3-bis(4,5-epoxypentoxy)-5-chlorobenzene; 1,4-bis(3,4-epoxybutoxy)-2-chlorocyclohexane; diglycidyl thioether; diglycidyl ether; 1,2,5,6-diepoxyhexane-3; 1,2,5,6-diepoxyhexane; those containing ester groups such as ERL 4221, a product of Dow Corporation, as illustrated in, for example, U.S. Pat. No. 4,814,103, the disclosure of which is hereby incorporated by reference, and mixtures thereof.

Other useful epoxides are listed in, for example, U.S. Pat. No. 3,298,998, the disclosure of which is hereby incorporated by reference. These compounds include but are not limited to those selected from the group consisting of bis[p-(2,3-epoxypropoxy)phenyl]cyclohexane; 2,2-bis[p-(2,3-epoxypropoxy)phenyl]norcamphane; 5,5-bis[(2,3-epoxypro-poxy)phenyl]hexahydro-4,6-methanoindane; 2,2-bis[4-(2,3-epoxypropoxy)-3-methylphenyl]hexahydro-4,7-methanoindane; and 2-bis[p-2,3-epoxypro-poxy)phenyl]-methylene-3-methylnorcamphane; and mixtures thereof. Other usable epoxides are found in, for example, Handbook of Epoxy Resin, Lee and Neville, McGraw-Hill, New York (1967) and U.S. Pat. No. 3,018,262, both of which are herein incorporated by reference.

Also, suitable epoxides for use in the present invention include the epoxidized dimer and trimer fatty acids, which are formed by epoxidizing the products of the polymerization of $C_{18}$ unsaturated fatty acids such as oleic acid, linoleic acid, linolenic acid, elaidic acid and the like. The use of a dimer or trimer fatty acid entity furnishes a higher molecular weight epoxide that is less likely to volatilize from the finished articles that the polyisocyanate compositions of the present invention are used to produce. The dimer fatty acid may have an acyclic, monocyclic, or bicyclic structure or comprise a mixture of compounds having different such structures.

Epoxidized mono-, di- and triglycerides prepared by epoxidation of the known unsaturated or partially unsaturated glycerides are preferred. The epoxidized glycerides may be prepared from any of the known fatty acid triglycerides available from natural or synthetic sources. The fatty acid group, which is connected to glycerol by an ester bond is usually a $C_6$–$C_{24}$ monocarboxylic acid (linear or branched; saturated, monounsaturated, or polyunsaturated). Such fatty acids and their equivalents are readily available at low cost from natural sources such as edible triglycerides. Specific illustrative fatty acids suitable for use include, but are not limited to, eicosanoic (arachidic) acid, heneicosanoic acid, docosanoic (behenic) acid, elaidic acid, tricosanoic acid, tetracosanoic (lignoceric) acid, caprylic acid, pelargonic acid, capric acid, caproic acid, lauric acid, palmitic acid, stearic acid, oleic acid, cetoleic acid, myristic acid, palmitoleic acid, gadoleic acid, erucic acid, rincinoleic acid, linoleic acid, linolenic acid, myristoleic acid, eleostearic acid, arachidonic acid, or mixtures or hydrogenated derivatives of these acids. The fatty acids may be derived synthetically or from natural sources such as triglyceride lipids. Mixtures of fatty acid entities, such as the mixtures of fatty acids typically obtained by hydrolysis (splitting) of a triglyceride are also suitable. These fatty acid triglycerides include, but are not limited to, fats and oils such as tallow, soybean oil, cottonseed oil, coconut oil, palm kernel oil, corn oil, fish oil, lard, butterfat, olive oil, palm oil, peanut oil, safflower seed oil, cocoa butter, sesame seed oil, rapeseed oil, sunflower seed oil, as well as fully or partially hydrogenated derivatives and mixtures of these triglycerides. Epoxidized linseed oil is particularly preferred.

The process according to the present invention can be carried out with a number of epoxidized triglycerides of vegetable or animal origin. The only requirement is that a substantial percentage of epoxide groups should be present. Thus, suitable epoxidized triglycerides are, for example, those containing from about 2 to about 10% by weight of epoxide oxygen. Products containing from about 4 to about 8.5% by weight of epoxide oxygen are particularly suitable. They can be produced from the following fats and oils: beef tallow, palm oil, lard, castor oil, peanut oil, rape oil, and, preferably, cottonseed oil, soybean oil, sunflower oil and linseed oil. Preferred starting materials are epoxidized soybean oil, epoxidized sunflower oil, epoxidized linseed oil and epoxidized train oil.

The quantity of acid scavenger to be used in accordance with the present invention generally ranges from about 10 to about 10,000 ppm, based on the weight of the polyisocyanate starting material. Acid scavenger is typically present in an amount of at least about 10 ppm, preferably of at least about 50 ppm, more preferably of at least about 100 ppm, and most preferably of at least about 150 ppm,. The quantity of acid scavenger is generally less than about 10,000 ppm, preferably less than about 5,000 ppm, more preferably less than about 2,000 ppm, and most preferably less than about 1,000 ppm, based on the weight of the polyisocyanate starting material. The quantity of acid scavenger present may be present in an amount ranging between any combination of these upper and lower ranges, inclusive, e.g. from 10 to 10,000 ppm, preferably from 50 to 5,000 ppm, more preferably from 100 to 2,000 ppm, and most preferably from 150 to 1,000 ppm, based on the weight of the polyisocyanate starting material.

Suitable catalysts for the carbodiimidization reaction of the isocyanate component in accordance with the present invention include but are not limited to catalysts of the phosphorous oxide type series such as, for example, commercially available mixtures of phospholine oxides, phospholene 1-oxides and phospholene 1-sulfides. Suitable phospholine oxides include, for example, those corresponding to the formulas:

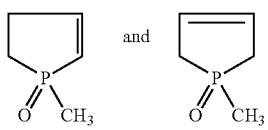

as are described in U.S. Pat. No. 5,202,358, the disclosure of which is hereby incorporated by reference. Other suitable catalysts which also known to be suitable carbodiimidization catalysts are described in, for example, U.S. Pat. No. 6,489,503, the disclosure of which is hereby incorporated by reference. As described therein, phospholene 1-oxides and phospholene 1-sulfides correspond to the formulas:

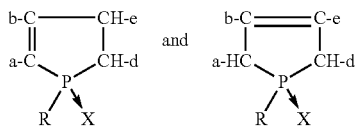

wherein a, b, c and d are each selected from the group consisting of hydrogen and hydrocarbyl from 1 to 12 carbon atoms inclusive, R is selected from the group consisting of lower alkyl and aryl and X is selected from the group consisting of oxygen and sulfur. The above phospholene compounds and methods for their preparation are described in U.S. Pat. Nos. 2,633,737, 2,663,738 and 2,853,473, the disclosures of which are hereby incorporated by reference. The 3-phospholenes can be isomerized readily to the corresponding 2-phospholenes by thermal treatment or by refluxing with an aqueous base as disclosed by Quin et al, Journal American Chemical Society, 33, 1024,1968. Representative compounds within the above class are 1-phenyl-2-phospholene-1-oxide; 3-methyl-1-phenyl-2-phospholene-1-oxide; 1-phenyl-2-phospholene-1-sulfide; 1-ethyl-2-phospholene-1-oxide; 1-ethyl-3-methyl-2-phospholene-1-oxide; 1-ethyl-3-methyl-2-phospholene-1-sulfide; and the isomeric phospholenes corresponding to the above named compounds. Also, polymer bound phospholene oxide may be employed specifically those having recurring units, for example, as disclosed in U.S. Pat. No. 4,105,643 and those of the following structure, as disclosed in U.S. Pat. No. 4,105,642, the disclosures of which patents are expressly hereby incorporated by reference. These recurring units are represented by the structure:

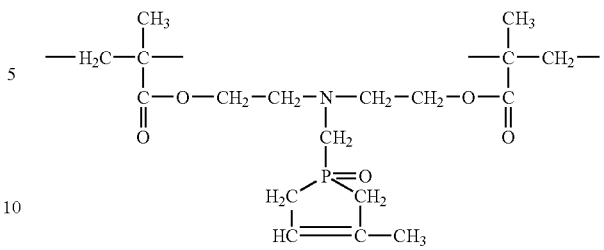

Also suitable are the diaza- and oxaza-phospholenes and —phosphorinanes described in U.S. Pat. No. 6,489,503 which correspond to the general formula:

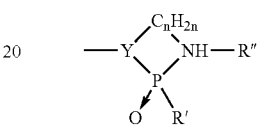

wherein $C_nH_{2n}$ represents alkylene from 1 to 12 carbon atoms, inclusive, at least one and not more than three adjacent carbon atoms and said alkylene radical forming a chain, one end of which is attached to Y, the other end of which is attached to N, thereby completing the heterocyclic ring; R' is selected from the group consisting of hydrocarbyl containing 1 to 12 carbon atoms, inclusive; and halo, nitro, alkoxy, alkyl, mercapto, and cyano substituted hydrocarbyl from 1 to 12 carbon atoms, inclusive; R" is hydrocarbyl containing from 1 to 12 carbon atoms, inclusive, and Y is selected from the group consisting of —O— and —NR"— wherein R" has the significance as defined above. The above compounds and methods for their preparation are described in U.S. Pat. No. 3,522,303, the disclosure of which is hereby incorporated by reference. Representative examples of such compounds are: 2-ethyl-1,3-dimethyl-1,3,2-diazaphospholane-2-oxide; 2-chloromethyl-1,3-dimethyl-1,3,2-diazaphospholane-2-oxide; 2-trichloromethyl-1,3-dimethyl-1,3,2-diazaphospholane-2-oxide; 2-phenyl-1,3-dimethyl-1,3,2-diazaphospholane-2-oxide; 2-phenyl-1,3-dimethyl-1,3,2-diaza-phosphorinane-2-oxide; 2-benzyl-1,3-dimethyl-1,3,2-diazaphospholane-2-oxide; 2-allyl-1,3-dimethyl-1,3,2-diazaphospholane-2-oxide; 2-bromomethyl-1,3-dimethyl-1,3,2-diazaphospholane-2-oxide; 2-cyclohexyl-1,3-dimethyl-1,3,2-diazaphospholane-2-oxide; 2-cyclohexyl-1,3-dimethyl-1,3,2-diaphospholane-2-oxide; 2-(2-ethoxyethyl)-1,3-dimethyl-1,3,2-diazaphospholane-2-oxide; and 2-naphthyl-1,3-dimethyl-1,3,2-diazaphospholane-2-oxide.

The quantity of catalyst used herein varies depending on the polyisocyanate starting material. Generally, it varies from about 0.1 to about 20 ppm, based on the weight of the polyisocyanate starting material. There is typically at least about 0.1 ppm, preferably at least about 0.5 ppm, and most preferably at least about 1 ppm of catalyst present, based on the weight of the polyisocyanate starting material. Also, there is generally no more than about 20 ppm, preferably no more than about 10 ppm, and most preferably no more than about 5 ppm of catalyst present, based on the weight of the polyisocyanate starting material. Of course, the quantity of catalyst present may be present in an amount ranging between any combination of these upper and lower ranges, inclusive, e.g. from 0.1 to 20 ppm, preferably from 0.5 to 10 ppm, and most preferably from 1 to 5 ppm, based on the weight of the polyisocyanate starting material.

Suitable catalysts stoppers or poisons to be used in accordance with the present invention include acids such as, for example, hydrohalic acids including, for example hydrogen chloride, hydrogen bromide, hydrogen fluoride, phosphoric acid and various chlorine-containing compounds including, for example, but not limited to aromatic and aliphatic acid chlorides such as, for example, benzoyl chloride, acetyl chloride and the like, chloroformates such as, for example, methyl chloroformate and the like, carbamoyl chlorides such as, for example, n-butyl carbamoyl chloride, the carbamoyl chloride precursors of MDI (diphenylmethane diisocyanate) and of the higher molecular weight homologues of MDI (i.e. PMDI or polyphenylmethylene polyphenylisocyanate), etc., zinc chloride, phosphoroxy chloride, phosphorous trichloride, sulfuryl chloride, silicon tetrachloride, etc. as described in, for example. U.S. Pat. No. 4,088,665, the disclosure of which is hereby incorporated by reference.

Also suitable are the sulfonyl isocyanates as described in, for example, U.S. Pat. No. 6,362,247, the disclosure of which is herein incorporated by reference. Among the sulfonyl isocyanates are, for example, inorganic or organic compounds which contain at least one structural unit corresponding to the following formula —SO$_2$—NCO. Organic sulfonyl isocyanates are preferably used, while those containing aromatically-bound isocyanatosulfonyl residues are particularly preferred. Processes for producing organic sulfonyl isocyanates of the type suitable for use in accordance with the invention and also their chemical behavior are comprehensively described by H. Ulrich in Chem. Rev. 65, pages 369–376,1965. In addition, the production of aryl sulfonyl isocyanates is described in U.S. Pat. Nos. 2,666,787 and 3,484,466, the disclosures of which are hereby incorporated by reference. According to the invention, it is possible to use aliphatic, cycloaliphatic and also aromatic mono- or polysulfonyl isocyanates, of which the following are mentioned by way of example: methyl sulfonyl isocyanate, butyl sulfonyl isocyanate, cyclohexyl sulfonyl isocyanate, chlorosulfone isocyanate, perfluorooctyl sulfonyl isocyanate, phenyl sulfonyl isocyanate, p-toluene sulfonyl isocyanate, benzyl sulfonyl isocyanate, p-chlorophenyl sulfonyl isocyanate, m-nitrophenylsulfonyl isocyanate, 2,5-dimethyl phenyl sulfonyl isocyanate, p-fluorophenyl sulfonyl isocyanate, 2,5-dichlorophenyl sulfonyl isocyanate, 3,4-dichlorophenyl sulfonyl isocyanate, p-bromophenyl sulfonyl isocyanate, p-methoxyphenyl sulfonyl isocyanate, p-nitrophenyl sulfonyl isocyanate and o-nitrophenyl sulfonyl isocyanate; m-phenylene disulfonyl diisocyanate, p-phenylene disulfonyl diisocyanate, 4-methyl-m-phenylene disulfonyl diisocyanate, 2-chloro-p-phenylene disulfonyl diisocyanate, 5-chloro-m-phenylene disulfonyl diisocyanate, 1,5-naphthylene disulfonyl diisocyanate, 3-nitro-p-phenylene disulfonyl diisocyanate, 4-methoxy-m-phenylene disulfonyl diisocyanate, 2,5-furandiyl-bis-(methylene-sulfonyl)-diisocyanate, 4,4'-bis-phenylene disulfonyl diisocyanate, 2,2'-dichloro-4,4'-biphenylylene-disulfonyl diisocyanate, 3,3'-dimethoxy-4,4'-biphenylylene-disulfonyl diisocyanate, (methylene-di-p-phenylene)-disulfonyl diisocyanate, (methylene-di-3,3'-dimethoxy-p-phenylene)-disulfonyl diisocyanate, (methylene-di-3,3'-dimethyl-p-phenylene)-disulfonyl diisocyanate and 2-methyl-p-phenylene disulfonyl diisocyanate; also sulfonyl isocyanates containing free NCO-groups such as m-isocyanatophenyl sulfonyl isocyanate, p-isocyanatophenyl sulfonyl isocyanate, 3-isocyanato-p-tolyl sulfonyl isocyanate, 5-isocyanato-o-tolyl sulfonyl isocyanate, 3-isocyanato-4-methoxyphenyl sulfonyl isocyanate, 4-isocyanato-3-chlorophenyl sulfonyl isocyanate, 4'-isocyanato-4-biphenylyl sulfonyl isocyanate, 4'-isocyanato-2,2'-dichloro-4-biphenylyl sulfonyl isocyanate, 4-isocyanato-3,3'-dimethoxy-4-biphenylyl sulfonyl isocyanate, α-(p-isocyanatophenyl)-p-tolyl sulfonyl isocyanate, α-(4-isocyanato-3-methoxyphenyl)-2-methoxy-p-tolyl sulfonyl isocyanate, α-(4-isocyanato-m-tolyl)-2,4-xylyl sulfonyl isocyanate and 5-isocyanato-1-naphthyl sulfonyl isocyanate; or containing free isothiocyanate groups such as p-isothiocyanatophenyl sulfonyl isocyanate, m-isothio-cyanatophenyl sulfonyl isocyanate, 3-isothiocyanate-4-methoxy phenyl sulfonyl isocyanate and 4-isothiocyanato-3-methyl phenyl sulfonyl isocyanate.

It is possible to use sulfonyl isocyanates wherein the —SO$_2$—NCO group is directly attached to an aromatic radical. Phenyl sulfonyl isocyanate, p-chlorophenyl sulfonyl isocyanate and p-toluene sulfonyl isocyanate (tosyl isocyanate) are particularly preferred. In addition to the organic sulfonyl isocyanates mentioned by way of example, it is also possible in accordance with the invention to use inorganic sulfonyl isocyanates such as chlorosulfonyl isocyanate or sulfonyl diisocyanate. Oxy-sulfonyl isocyanates such as trimethyl silyloxy-sulfonyl isocyanate are also suitable.

Another suitable group of acids for the present invention is the silylated acids which correspond to the general formula:

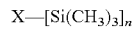

X—[Si(CH$_3$)$_3$]$_n$ wherein:
X: represents the neutral acid residue obtained by the removal of the acidic hydrogen atoms from an n-basic acid having a pK$_a$ value of at most 3, and
n: represents an integer of 1 to 3.

These silylated acids are indeed the preferred catalyst stopper or poison.

In these silylated acids, it is preferred that X is the neutral acid residue of an oxygen-containing acid which bears n acid hydrogen atoms and has a maximum pK$_a$ value of 2. Some examples of such suitable acids include compounds such as, but not limited to, the corresponding silylated sulfonic acids such as, for example, trifluoromethanesulfonic acid trimethylsilylester or methanesulfonic acid trimethylsilyl ester, or silylated esters of acids of phosphorus, such as phosphoric acid tris(trimethylsilyl ester) and/or phorphoric acid diethyl ester trimethylsilyl ester. Such compounds are described in U.S. Pat. No. 5,202,358 and U.S. Pat. No. 6,362,247, the disclosures of which are hereby incorporated by reference.

The quantity of acid used herein generally is between about 1 and about 200 ppm, based on the weight of the polyisocyanate starting material. There is typically at least about 1 ppm, preferably at least about 5 ppm and most preferably at least about 10 ppm of acid present, based on the weight of the polyisocyanate starting material. Also, there is generally no more than about 200 ppm, preferably no more than about 100 ppm and most preferably no more than about 50 ppm of acid present, based on the weight of the polyisocyanate starting material. Of course, the quantity of stopper or poison present may be present in an amount ranging between any combination of these upper and lower ranges, inclusive, e.g. from 1 to 200 ppm, preferably from 5 to 100 ppm, and most preferably from 10 to 50 ppm, based on the weight of the polyisocyanate starting material.

In accordance with the present invention, neutralization of any acidic impurities in the organic isocyanate is achieved by addition of an acid scavenger as described herein above.

This can be accomplished at room temperature; however, it is generally carried out at elevated temperatures between 40 to 100° C. to accelerate the process. Typically, the neutralization takes place within about 5 to about 300 minutes in a well stirred vessel. It may also take place in a column when, for example, the materials are passed through the column which contains the solid basic materials.

The carbodiimidization reaction according to the invention is generally carried out at a temperature in the range from about 50° C. to about 150° C. and preferably at a temperature in the range from 60° C. to 100° C. The optimal reaction temperature depends on the starting isocyanates used and may be determined in a simple preliminary test.

The carbodiimidization reaction is generally terminated on reaching a degree of carbodiimidization (degree of carbodiimidization is the percentage of carbodiimidized isocyanate groups, based on the total quantity of isocyanate groups present in the starting isocyanate) of about 3 to about 35% (preferably 5 to 30%) by weight. The degree of carbodiimidization is reflected in the quantity of carbon dioxide escaping from the reaction mixture during the process according to the invention. Accordingly, this volumetrically measurable quantity of carbon dioxide provides information on the degree of carbodiimidization reached at any stage during the process according to the invention.

In a preferred embodiment of the present invention wherein the polyisocyanate starting materials comprises monomeric MDI (i.e. diphenylmethane diisocyanate) and optionally higher homologues thereof (i.e. polymeric MDI), the isocyanate content of the final product is 23 to 32%, preferably 26.5 to 31% and most preferably 28.5 to 30%.

The isocyanate mixtures of the present invention comprise monomeric diphenylmethane diisocyanate, carbodiimide, uretonimine, and higher homologues of carbodiimides and/or uretonimines, and epoxide. The monomeric MDI present in this mixture ranges from about 60% to less than about 90% by weight, based on 100% by weight of the total isocyanate mixture, and the balance, i.e. from more than 10% to about 40% by weight, comprises carbodiimide, uretonimine, and higher molecular weight homologues of carbodiimides and/or uretonimines. In the context of the present invention, these higher molecular weight homologues comprise molecules which contain from two to six incorporated carbodiimide and/or uretonimine groups. Only a very small amount of the total weight of the mixture comprises an epoxide, a catalyst and a catalyst stopper. The mixture preferably comprises from 70% to 80% by weight and most preferably from 72% to 78% by weight of monomeric MDI, based on 100% by weight of the total isocyanate mixture. The balance of the mixture comprises from 20% to 30% by weight and most preferably from 22% to 28% by weight, based on 100% by weight of the total isocyanate mixture.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

The following components were used in the working examples of the present application:

Isocyanate A: diphenylmethane diisocyanate having an NCO group content of about 33.6% and comprising about 99% of the 4,4'-isomer and about 1% of the 2,4'-isomer; and having an acidity value of 7 as determined by ASTM D-5629.

Isocyanate B: diphenylmethane diisocyanate having an NCO group content of about 33.6% and comprising about 99% of the 4,4'-isomer and about 1% of the 2,4'-isomer; and having an acidity value of 20 as determined by ASTM D-5629.

Isocyanate C: diphenylmethane diisocyanate having an NCO group content of about 33.6% and comprising about 99% of the 4,4'-isomer and about 1% of the 2,4'-isomer; and having an acidity value of 4 as determined by ASTM D-5629.

Epoxide A: polyepoxide based upon linseed oil and having an epoxide equivalent weight of about 180; commercially available as Epoxol 9–5 from Unitech Chemical Inc.

Catalyst A: 1-methyl-3-phospholene-1-oxide

Acid A: trimethylsilyl trifluoromethane sulfonate

The following experiments were conducted to illustrate the effect of an acid scavenger on decreasing the time and/or catalyst level needed for completion of the carbodiimidization of monomeric MDI to 29.5% NCO. The following procedure was used to prepare CD Isocyanate 1 and CD Isocyanate 3.

Procedure:

CD Isocyanate was prepared by adding 100 pbw of the Isocyanate tested to a reaction vessel and heating to 80° C. under flowing nitrogen. In the examples representative of the present invention, 1000 ppm of Epoxide A was added to the isocyanate and the mixture was stirred at 80° C. for 1 hour. (No epoxide was added in the comparative examples.) While at 80° C., 2.5 ppm of Catalyst A (1-methyl-3-phospholene-1-oxide, i.e. PHO) was added. The reaction progressed and was monitored by titration and/or refractive index until the desired % NCO was reached. At this point 32.5 ppm, based on the weight of the starting isocyanate component, of Acid A, a catalyst poison, i.e. trimethylsilyl trifluoromethane sulphonate (TMST) was added. The TMST was stirred into the reaction and then the vessel was cooled to room temperature. The time required to reach the desired % NCO was affected by three factors: (i) catalyst level, (ii) temperature, and (iii) acidity of the monomeric MDI. Higher levels of MDI acidity resulted in an increased (i.e. longer) reaction time.

The acidity of the starting isocyanate was determined in accordance with ASTM D 5629.

Results:

Example 1

(Comparative) Isocyanate A (having an initial acidity of about 7 ppm) was used to prepare CD Isocyanate 1 in accordance with the above procedure, without the addition of epoxide. The reaction reached completion, as measured by a % NCO of about 29.5%, in about 490 minutes. This product is referred to as CD Isocyanate 1.

Example 2

Isocyanate C (having an initial acidity of about 4) was used to prepared CD Isocyanate 2 in accordance with the above procedure. After the addition of Isocyanate C to the reaction vessel, 1000 ppm Epoxide A was added to 100 pbw of Isocyanate C, and allowed to react at 80° C. for 1 hour. While at 80° C., 1.0 ppm of Catalyst A was added. Even with such a low level of catalyst, the reaction was completed in 400 minutes. This product is referred to as CD Isocyanate 2.

Example 3

(Comparative) Isocyanate B (having an initial acidity of about 20 ppm) was used to prepare CD Isocyanate 3. Epoxide was not added to Isocyanate B in the preparation of CD Isocyanate 3. A conventional CD isocyanate was made as described in Example 1 above, which is also a comparative example. After 365 minutes, the NCO group content was only 32.65. The run was stopped at this point, but extrapolation of this data indicated an estimated time to completion of approximately 1,000 minutes. This product is referred to as CD Isocyanate 3.

Example 4

In this example, Isocyanate B which had an initial acidity of 20 ppm was used as the starting polyisocyanate. In addition, 1000 ppm of Epoxol 9–5 was added to 100 pbw of Isocyanate B. As in Example 2 above, Epoxol 9–5 was added while the MDI was being heated to about 80° C., and allowed to react for 1 hour before the addition of Catalyst A. Surprisingly, this run reached completion (to a % NCO of about 29.5%) only 180 minutes after the addition of the Catalyst. This product is referred to as CD Isocyanate 4.

TABLE 1

| Isocyanate | Example 1 A | Example 2 C | Example 3 B | Example 4 B |
|---|---|---|---|---|
| Isocyanate (pbw) | 100.0 | 100.0 | 100.0 | 100.0 |
| Initial % NCO of Isocyanate | 33.6 | 33.6 | 33.6 | 33.6 |
| Acidity (ppm) | 7 | 4 | 20 | 20 |
| Epoxide A (% by wt.)[1] | 0% | 0.1% | 0% | 0.1% |
| Catalyst A (ppm) | 2.5 | 1.0 | 2.5 | 2.5 |
| Acid A (ppm) | 32.5 | 13.5 | 32.5 | 32.5 |
| Product | CD Iso 1 | CD Iso 2 | CD Iso 3 | CD Iso 4 |
| Time to reach 29.5% % NCO (mins) | 490 | 400 | 1,000[2] | 180 |

[1] % by wt. of epoxide based on the weight of the starting polyisocyanate
[2] estimated based on reaction rate over first 10 hrs of reaction Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A process for the preparation of liquid storable organic isocyanates containing carbodiimide and/or uretoneimine groups, comprising:
   (1) neutralizing acidic impurities in an organic isocyanate with an acid scavenger, in which the organic isocyanate comprises polymethylene polyphenylisocyanate comprising 90 to 100% by weight of diphenylmethane diisocyanate and 0 to 10% by weight of higher functional polyisocyanates of the diphenylmethane series, wherein the diphenylmethane diisocyanate comprises from 96 to 100% by weight of the 4,4'-isomer, from 0 to 1% by weight of the 2,2'-isomer and from 0.1 to 4% by weight of the 2,4'-isomer, with the %'s by weight of the 4,4'-isomer, the 2,2'-isomer and the 2,4'-isomer totaling 100% by weight of monomeric diphenylmethane diisocyanate,
   (2) partially carbodiimidized isocyanate groups of the neutralized organic isocyanate with a phosphorous oxide catalyst and
   (3) terminating the carbodiimidization reaction by the addition of an acid comprising a silylated acid corresponding to the formula:

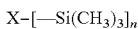

wherein:
      X: represents the neutral acid residue obtained by removal of the acidic hydrogen atoms from an n-basic acid having a pKa value of at most 3, and
      n: represents an integer of 1 to 3.
2. A process for the preparation of liquid storable organic isocyanates containing carbodiimide and/or uretoneimine groups, comprising:
   (1) neutralizing acidic impurities in an organic isocyanate with an acid scavenger, in which the organic isocyanate comprises polymethylene polyphenylisocyanate comprising 80 to 100% by weight of diphenylmethane diisocyanate and 0 to 20% by weight of higher functional polyisocyanates of the diphenylmethane series, wherein the diphenylmethane diisocyanate comprises from 40 to 80% by weight of the 4,4'-isomer, from 0 to 8% by weight of the 2,2'-isomer and from 20 to 60% by weight of the 2,4'-isomer, with the %'s by weight of the 4,4'-isomer, the 2,2'-isomer and the 2,4'-isomer totaling 100% by weight of monomeric diphenylmethane diisocyanate, and the acid scavenger is selected from the group consisting of epoxides, sodium carbonate sodium bicarbonate calcium carbonate potassium carbonate, potassium bicarbonate and calcium hydroxide,
   (2) partially carbodiimidizing isocyanate groups of the neutralized organic isocyanate with a phosporous oxide catalyst, and
   (3) terminating the carbodiimidization reaction by the addition of an acid comprising a silylated acid corresponding to the formula:

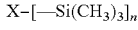

wherein:
      X: represents the neutral acid residue obtained by removal of the acidic hydrogen atoms from an n-basic acid having a pKa value of at most 3. and
      n: represents an integer of 1 to 3.
3. The process of claim 1, wherein said organic polyisocyanate comprises 100% diphenylmethane diisocyanate wherein the 4,4'-isomer comprises from 96 to 100% by weight, the 2,2'-isomer comprises from 0 to 1% by weight, and the 2,4'-isomer comprises from 0.1 to 4% by weight, with the %'s by weight of the 4,4'-isomer, the 2,2'-isomer and the 2,4'-isomer totaling 100% by weight.
4. The process of claim 1, wherein said epoxide comprises epoxidized linseed oil.
5. The process of claim 1, wherein said phosphorous oxide catalyst comprises a phospholene oxide.
6. The process of claim 5, wherein said phospholene oxide catalyst comprises 1-methyl-3-phospholene oxide.
7. The process of claim 1, wherein the silylated acid comprises trimethylsilyl trifluoromethylsulfonate.
8. The process of claim 1, wherein the acid in (3) is present in an amount of 1 to 200 ppm, based on the weight of the polyisocyanate starting component.

9. The process of claim 1, wherein the acid scavenger comprises a liquid epoxy compound.

10. The process of claim 9, wherein the liquid epoxy compound comprises an aliphatic epoxy compound.

11. The process of claim 10, wherein the aliphatic epoxy compound comprises an aliphatic epoxidized oil.

12. The process of claim 1, wherein the acid scavenger is present in an amount of from 10 to 10,000 ppm, based on the weight of the polyisocyanate starting component.

13. The process of claim 2, wherein the acid scavenger is an epoxide comprising epoxidized linseed oil.

14. The process of claim 2, wherein said phosphorous oxide catalyst comprises a phospholene oxide.

15. The process of claim 14, wherein said phospholene oxide catalyst comprises 1-methyl-3-phospholene oxide.

16. The process of claim 2, wherein the silylated acid comprises trimethylsilyl trifluoromethylsulfonate.

17. The process of claim 2, wherein the acid in (3) is present in an amount of 1 to 200 ppm, based on the weight of the polyisocyanate starting component.

18. The process of claim 2, wherein the acid scavenger is an epoxide comprising an aliphatic epoxy compound.

19. The process of claim 18, wherein the aliphatic epoxy compound comprises an aliphatic epoxidized oil.

20. The process of claim 2, wherein the acid scavenger is present in an amount of from 10 to 10,000 ppm, based on the weight of the polyisocyanate starting component.

21. A process for the preparation of liquid storable organic isocyanates containing carbodiimide and/or uretoneimine groups, comprising:
   (1) neutralizing acidic impurities in an organic isocyanate with an acid scavenger, in which the acid scavenger comprises an aliphatic epoxidized oil,
   (2) partially carbodiimidizing isocyanate groups of the neutralized organic isocyanate with a phosphrorous oxide catalyst, and
   (3) terminating the carbodiimization reaction by the addition of an acid.

* * * * *